United States Patent
Melton, Jr. et al.

[11] Patent Number: 5,373,848
[45] Date of Patent: Dec. 20, 1994

[54] ULTRASONIC TIME-DOMAIN METHOD FOR SENSING FLUID FLOW

[75] Inventors: Hewlett E. Melton, Jr., Montclair; King-Wah W. Yeung, Cupertino; Michael Greenstein, Los Altos, all of Calif.

[73] Assignee: Hewlett-Packard Company, Palo Alto, Calif.

[21] Appl. No.: 104,514

[22] Filed: Aug. 9, 1993

[51] Int. Cl.$^5$ .............................................. A61B 8/06
[52] U.S. Cl. ............................. 128/661.09; 73/861.25
[58] Field of Search ..................... 128/661.07–661.10; 73/861.25; 367/104, 105

[56] References Cited

U.S. PATENT DOCUMENTS

| | | | |
|---|---|---|---|
| 4,608,993 | 9/1986 | Albert | 73/861.25 |
| 4,944,189 | 7/1990 | Nakajima et al. | 128/660.01 |
| 5,018,528 | 5/1991 | Morita et al. | 128/661.09 |
| 5,109,857 | 5/1992 | Roundhill et al. | 128/660.07 X |

*Primary Examiner*—Francis Jaworski
*Attorney, Agent, or Firm*—Jeffrey Slusher

[57] ABSTRACT

Pulses of ultrasound are focused in the patient's body to create an interrogation volume where either the magnitude of velocity or the direction of blood flow is to be measured. The strength of the back-scattered signal is measured for each pulse and the mean squared rate of change of the envelope of the range-gated signal is estimated. In order to measure flow velocity independent of direction, the interrogation volume is generated substantially as a sphere by creating an ultrasonic wave envelope in which the components of the mean square spatial gradient are equal in all directions. The estimated mean square rate of change of the envelope of the back-scattered signal is then scaled to provide a direction-independent measurement of flow velocity. In order to determine the direction of flow, the interrogation volume is generated substantially as an ellipsoid. The long axis of the ellipsoidal interrogation volume is then rotated until the measured mean square rate of change of the envelope of the return signal is at a minimum, which is reached when the long axis is aligned with the flow direction. The interrogation volume is preferably rotated and translated using differential phasing of the ultrasonic signals from different transducer elements in a two-dimensional phased array.

7 Claims, 8 Drawing Sheets

ULTRASONIC TIME-DOMAIN METHOD FOR SENSING FLUID FLOW

BACKGROUND OF THE INVENTION

1. Technical Field

This invention involves a method for using ultrasound to sense the speed and direction of flow of a fluid, such as blood in a coronary artery.

2. Description of the Related Art

The measurement of blood flow in the coronary arteries is a well-known technique for diagnosing coronary artery diseases. There are, consequently, many different devices and methods for determining this blood flow.

One common sensing technique involves the use of ultrasound. Using this technique, ultrasound is directed into the body of the patient and tiny particles such as red blood cells, which are suspended in the blood, scatter the ultrasonic energy back towards the transducer. The transducer then converts the back-scattered ultrasonic energy into an electrical signal that is processed in some known manner to determine an estimate of the flow.

One great advantage of ultrasonic sensing is that it is non-invasive, meaning that it can be carried out without having to cut or insert anything into the patient's body. A problem one faces when using existing ultrasonic flow measurement techniques, however, is that measurements are often made through the "keyhole" between the ribs in a transthoracic scan, where the coronary arteries typically twist over the curved surface of the moving heart wall. The direction of the blood in the arteries or the motion of the heart wall with respect to the line-of-sight of the ultrasonic beam is therefore usually not known. This is a serious problem for the many common techniques that use the principle of Doppler shift.

The Doppler principle used in existing techniques for calculating flow velocity v based on the frequency shift of ultrasonic waves scattered by moving red cells can be expressed as follows:

$$f_d = 2\left(\frac{v}{c}\right)f_0 \cdot \cos\theta,$$

in which $f_0$ is the frequency of the ultrasonic wave sent into the body, v is the flow velocity, c is the speed of sound, $\theta$ is the angle between the line-of-sight direction of the beam and the flow, and $f_d$ is the detected frequency shift of the signal that returns to the transducer. As long as $\cos \theta$ is not equal to zero, the frequency shift will increase with increasing flow velocity.

As the equation shows, it is not possible using conventional Doppler techniques to detect any frequency shift if $\theta$ equals 90°, that is, if the flow is perpendicular to the line-of-sight of the ultrasonic transducer, regardless of how fast the blood is flowing. Police officers who use radar guns to check for speeders are a more common example of this problem: the officers cannot position themselves at right angles to the cars being checked because the typical radar gun uses the same Doppler principle and would tell the disbelieving police officers that the cars were not moving at all.

If the direction of flow is at an angle of 60° from the line-of-sight of the ultrasonic transducer, the indicated frequency shift will be only half what it would be if the flow and the line-of-sight were parallel. In general, the angle $\theta$ is not known beforehand. In the context of blood-flow measurements, what is needed is therefore a technique that is substantially isotropic, that is, direction-independent. Alternatively, a technique is needed that determines the direction of flow so that Doppler measurements can be adjusted accordingly. This invention provides such techniques.

SUMMARY OF THE INVENTION

According to the invention, pulses of ultrasound are focused in the patient's body to create an interrogation volume where blood flow is to be measured. The strength of the back-scattered signal is then measured for each pulse and the mean squared rate of change of the envelope of the return signal is estimated.

In order to measure flow velocity independent of direction, the interrogation volume is generated substantially as a sphere. This is done by creating an ultrasonic interrogation volume in which the range dimension, which is determined by the number of excitation cycles, is set equal to the lateral dimensions (azimuth and elevation). In particular, an ultrasonic envelope is generated in which the components of the mean square gradient of the interrogation wave envelope are equal. The estimated mean square rate of change of the envelope of the back-scattered signal is then scaled to provide a direction-independent measurement of the magnitude of the flow velocity.

In order to determine the direction of flow, the interrogation volume is generated substantially as an ellipsoid. The long axis of the ellipsoidal interrogation volume is then rotated until the measured mean square rate of change of the envelope of the return signal is at a minimum, which is reached when the long axis is aligned with the flow direction. The interrogation volume is preferably rotated and translated using differential phasing of the ultrasonic signals from different transducer elements in a two-dimensional phased array.

DETAILED DESCRIPTION

This invention provides a method for determining the speed and direction of flow of a fluid within any conduit as long as the fluid contains some form of particles or discontinuities that are able to scatter ultrasonic waves. The invention is, however, particularly well suited for solving the problems, described above, that are connected with determining the flow of blood within a blood vessel such as a coronary artery, and also within other organs of the body. Accordingly, the discussion below is directed to this application.

Figure 1:
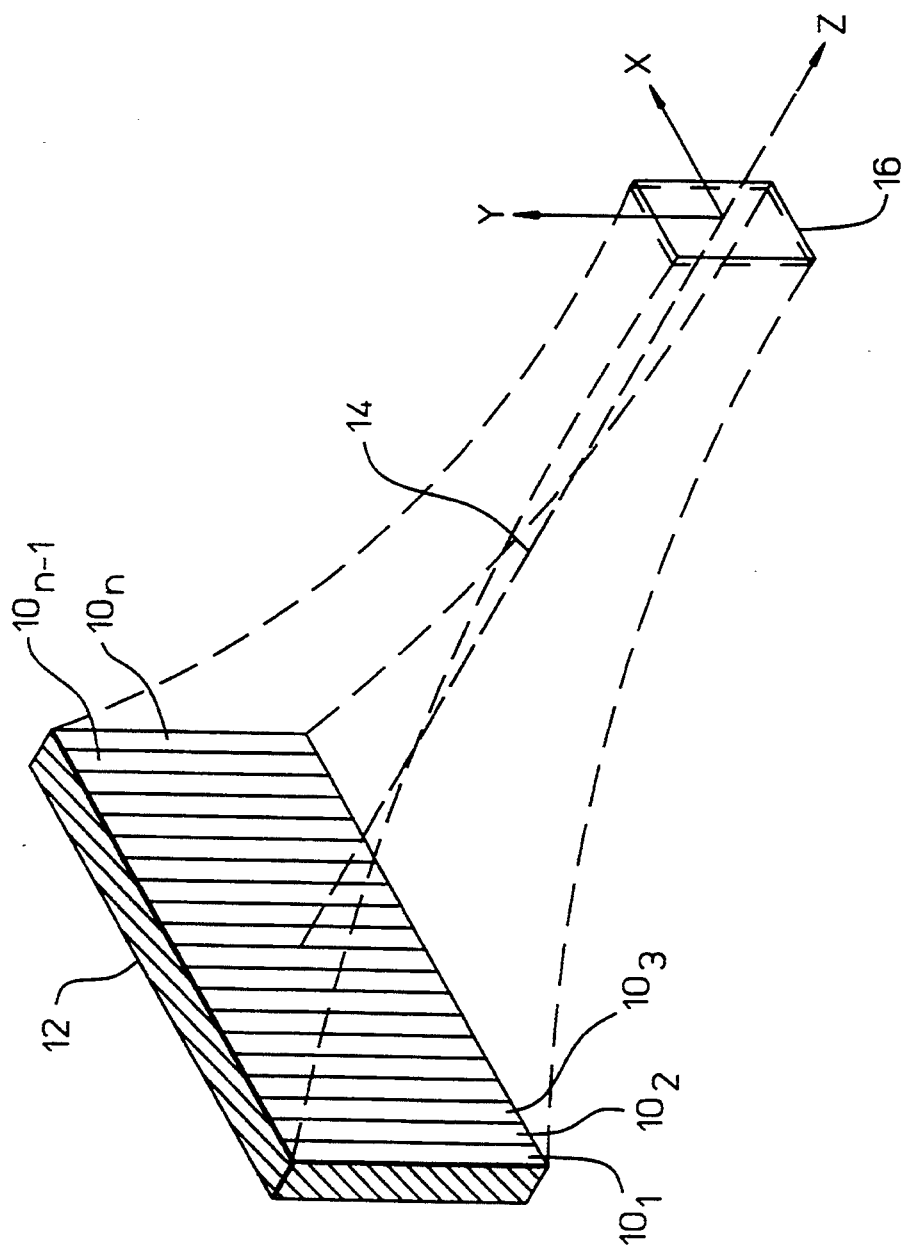
FIG. 1 illustrates an anisotropic interrogation volume (AIV) generated by a 1-D phased array of ultrasonic transducer elements as found in the prior art.

FIG. 1 illustrates the principle of operation of a conventional one-dimensional phased array of ultrasonic transducer elements that are used to estimate fluid flow. In such devices, several ultrasonic transducer elements $10_1, 10_2, 10_3, \ldots, 10_{n-1}, 10_n$, are mounted or manufactured as a parallel array 12. The transducer elements are individually excited using known circuitry and techniques to generate a pattern of ultrasonic waves that propagate principally along an interrogation direction 14, which can be steered over a range of angles relative to the normal to the plane of the phased array 12.

The signals from the various transducer elements $10_1, \ldots, 10_n$ are phased using known techniques so that they focus to create a region of maximum constructive interference where one wishes to measure the fluid flow. This region in known as the interrogation volume. In FIG. 1, the anisotropic interrogation volume (AIV) created by such a conventional 1-D phased array 12 is indicated as the thin, substantially rectangular AIV region 16.

Existing ultrasonic imaging techniques such as the one illustrated in FIG. 1 employ bursts of ultrasonic waves with the shortest possible duration in order to achieve high range resolution in the image. Because the lateral dimensions of the ultrasonic beam are limited by the physical dimensions of the transducer elements $10_1, 10_2, \ldots, 10_n$, these techniques often cause the anisotropism, that is, the direction-dependence, of the interrogation volume 16.

In FIG. 1, the boundaries of the ultrasonic beam are shown as the $-6$ dB boundaries of signal strength and the lengths of the "edges" are not equal. For typical conventional systems with the configuration illustrated in FIG. 1, the range dimension (z-axis) of the interrogation volume 16 is typically less than 1 mm because of the short pulse length used, while the azimuthal dimension (x-axis) is about 3 mm and the dimension in the elevational direction (y-axis) is roughly 5 mm.

The anisotropism of the conventional interrogation volume causes the signal returned to the transducer to have characteristics that depend on the orientation of the interrogation beam and the direction of flow of the fluid to be measured. In other words, if the fluid is flowing in the x-direction, the system will indicate that its speed is different than if it were flowing in the z-direction, even if the speed is the same. The cause of this problem is discussed above when it comes to the Doppler techniques commonly used.

Figure 2:
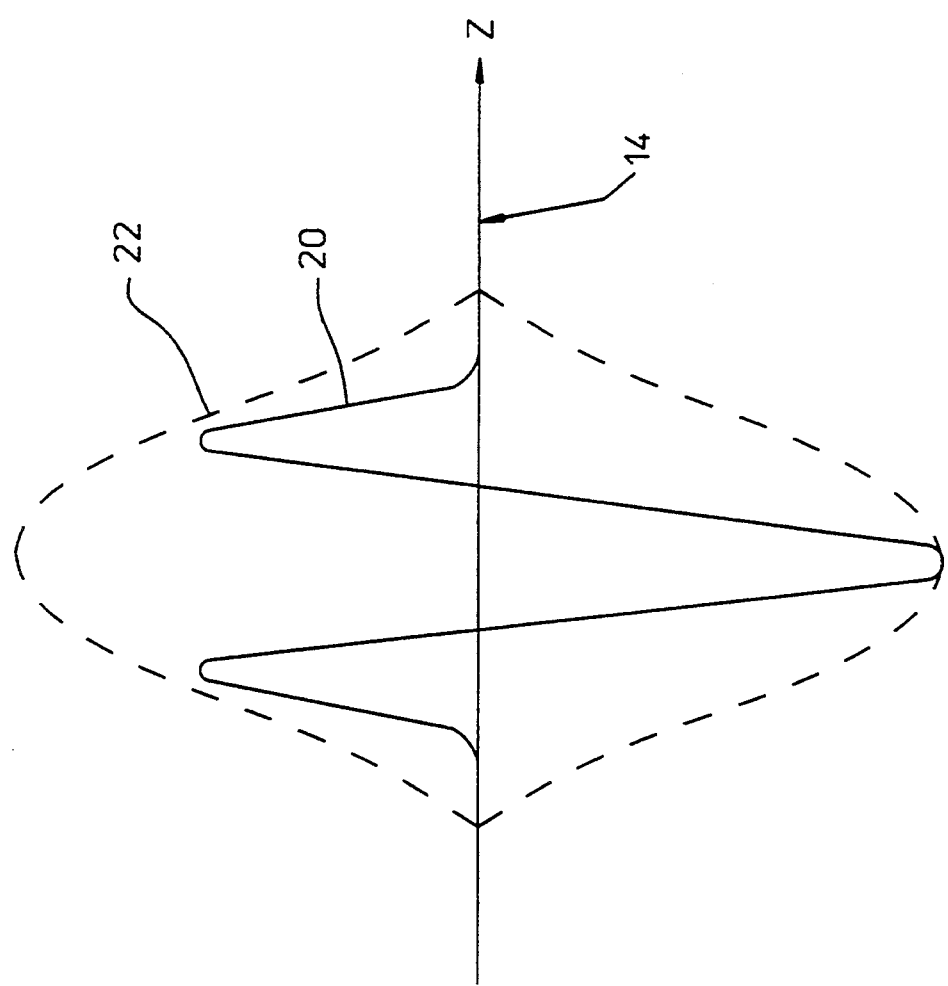
FIG. 2 illustrates a wave and envelope for a conventional anisotropic interrogation volume (AIV).

FIG. 2 shows a wave and envelope along the range direction (z-axis) used to produce an AIV. In order to increase image resolution, a typical conventional imaging transducer with an AIV has only one or two cycles within the interrogation volume. In FIG. 2, 1½ cycles of the interrogation pulse 20 define the wave envelope 22 of the AIV.

As is well known, the pulse 20 will be scattered back towards the transducer array 12 (FIG. 1) by each of the particles within the fluid, such as red blood cells in an artery. The back-scattered pulses thereby undergo Doppler shift. Using the Doppler relationship shown above, the degree of frequency shift is then used to calculate fluid flow. As is discussed above, however, the degree of frequency shift in such conventional systems depends on the angle between the direction of fluid flow and the interrogation direction 14.

In ultrasonic flow-measuring systems, the waves of ultrasound are typically transmitted at a constant pulse repetition frequency (PRF); this is also preferred according to this invention since it leads naturally to constant sampling rates for the return signal. The signal that returns to the ultrasonic transducer, either at a fixed time delay or, equivalently, at a fixed distance from the transducer, after the generation of each burst, is produced by the scattering of a large number of particles that lie inside the interrogation volume. In the interrogation volume, the envelope of the ultrasonic signal along the direction of wave propagation is primarily determined from the envelope of the burst (the length) as a function of time; the cross-sectional area is determined by the transducer transmit and receive beam forming in a plane perpendicular to the propagation direction.

According to the invention, the length of the interrogation volume is generated so that it is the same as the width and height of the beam. The interrogation volume is then approximately spherical. In particular, the interrogation volume is generated so that the components of the mean square gradient of the interrogation wave envelope are substantially equal. The interrogation volume is then approximately spherical in the sense used in this invention. As is shown below, the measurement of flow velocity within the spherical interrogation volume (SIV) is thereby made independent of the direction of fluid flow.

To illustrate this new approach, consider a wave envelope S that defines the interrogation volume. The wave envelope S is a function of both the transmitted and received ultrasonic beam properties. The detected envelope of the return signal is proportional to S. In the most general case, the wave envelope changes in all three directions (x, y, z) in space and it also changes shape over time. The wave envelope is thus a function of both position and time. In other words:

$$S = f(x, y, z, t) \qquad \text{Eqn. 1}$$

The total differential dS of the wave envelope reflects changes in the wave envelope:

$$dS = \frac{\partial S}{\partial x} dx + \frac{\partial S}{\partial Y} dy + \frac{\partial S}{\partial z} dz + \frac{\partial S}{\partial t} dt \qquad \text{Eqn. 2}$$

Dividing both sides of Eqn. 2 by dt leads to:

$$\frac{dS}{dt} = \frac{\partial S}{\partial x} v_x + \frac{\partial S}{\partial y} v_y + \frac{\partial S}{\partial z} v_z + \frac{\partial S}{\partial t} \qquad \text{Eqn. 3}$$

where $v_x = \frac{dx}{dt}$; $v_y = \frac{dy}{dt}$; $v_z = \frac{dz}{dt}$

The terms $v_x$, $v_y$, and $v_z$ are the component velocities in the x, y, and z directions, respectively, of the moving particles within the infinitesimally small portion dS of the interrogation volume. This equation derives from the continuity of the interrogation signal within the interrogation volume.

Assume now that one generates a stationary interrogation volume that has a steady wave envelope, that is, assume there are no local sources or sinks of the acoustic signal, and and all ultrasound comes from the transducer. Then:

$$dS/dt = 0 \qquad \text{Eqn. 4}$$

Since the envelope of the return signal is proportional to the wave envelope S, the rate of change of the envelope of the return signal from the interrogation volume can be expressed as:

$$\frac{\partial S}{\partial t} = -\frac{\partial S}{\partial x} v_x - \frac{\partial S}{\partial y} v_y - \frac{\partial S}{\partial z} v_z \qquad \text{Eqn. 5}$$

Note that the constant of proportionality between the envelope of the return signal and the wave envelope S would appear on both sides of Eqn. 5 and would cancel.

Consider now the mean square rate of change of the envelope of the return signal from the interrogation volume:

$$\overline{\left(\frac{\partial S}{\partial t}\right)^2} = \overline{\left(\frac{\partial S}{\partial x}\right)^2} v_x^2 + \overline{\left(\frac{\partial S}{\partial y}\right)^2} v_y^2 + \overline{\left(\frac{\partial S}{\partial z}\right)^2} v_z^2 + \overline{\text{cross terms}} \qquad \text{Eqn. 6}$$

In this expression, the cross terms include the products of velocity terms and spatial rates along different axes (x-y, x-z, y-z). These signals from along different axes are uncorrelated. Because the wave-scattering is a random process, the mean value of these cross terms therefore approaches zero and can be ignored at this level of approximation.

Assume now further that the component velocities $v_x$, $v_y$, and $v_z$ are constant. In other words, assume that the fluid neither speeds up nor slows down within the interrogation volume, although one does not necessarily know in which direction it is flowing. The previous equation can then be written in the following form:

$$\overline{\left(\frac{\partial S}{\partial t}\right)^2} = \overline{\left(\frac{\partial S}{\partial x}\right)^2} v_x^2 + \overline{\left(\frac{\partial S}{\partial y}\right)^2} v_y^2 + \overline{\left(\frac{\partial S}{\partial z}\right)^2} v_z^2 \qquad \text{Eqn. 7}$$

According to the invention, in order to determine blood flow independent of direction, the interrogation volume is made substantially spherical. For this case, this means that the volume is symmetric with respect to the spatial gradient along any axis that passes through its center (not just the x-y-z system shown in the figures).

This can be expressed as:

$$\overline{\left(\frac{\partial S}{\partial x}\right)^2} = \overline{\left(\frac{\partial S}{\partial y}\right)^2} = \overline{\left(\frac{\partial S}{\partial z}\right)^2} = G \qquad \text{Eqn. 8}$$

or, using vector notation, $$\overline{(\nabla S_i)^2} = G$$

where $\nabla S_i$ is the i'th component of the gradient of S, and G is a constant.

The expression for the mean square rate of change of the envelope of the return signal from the stationary SIV can then be expressed as:

$$\overline{\left(\frac{\partial S}{\partial t}\right)^2} = G \cdot (v_x^2 + v_y^2 + v_z^2) = G|v|^2 \qquad \text{Eqn. 9}$$

where G is a constant proportionality factor.

In other words, the mean square rate of change of the envelope of the return signal from the stationary SIV according to the invention is proportional to the square of the magnitude of the flow velocity v, but is independent of its direction. The condition expressed by Eqn. 8 holds true for any arbitrary set of orthogonal axes.

Using the SIV according to the invention, one therefore senses the envelope of the return signal from the SIV using known methods and then uses known numerical techniques to calculate the mean square rate of change of that signal. For example, in order to determine an estimate of the instantaneous rate of change ($\partial S/\partial t$) for the envelope of the return signal S at time $t=t_m$ (at the m'th pulse from some beginning time), the system's processing circuitry can subtract from the current measured value of S the immediately preceding value and then divide by the sampling period (time scaling may also be carried out in later steps). The system can then square and sum each of these difference values after a predetermined number N of measurement values, and then average the squared differences by dividing by (N−1).

The constant G, which acts a proportionality factor that relates the mean square rate of change of the envelope of the return signal to the magnitude of the velocity, may be determined when the system is calibrated either by experiment (using known flow velocities) or by theoretical calculations based on the characteristics of the chosen transducer array used to generate the SIV and the parameters of the chosen wave envelope for the interrogation volume. In order to obtain a measure of the magnitude $|v|$ of the flow velocity v, the system then divides the numerically determined mean square rate of change of the return signal by the constant G and takes the square root of the result.

Figure 3:
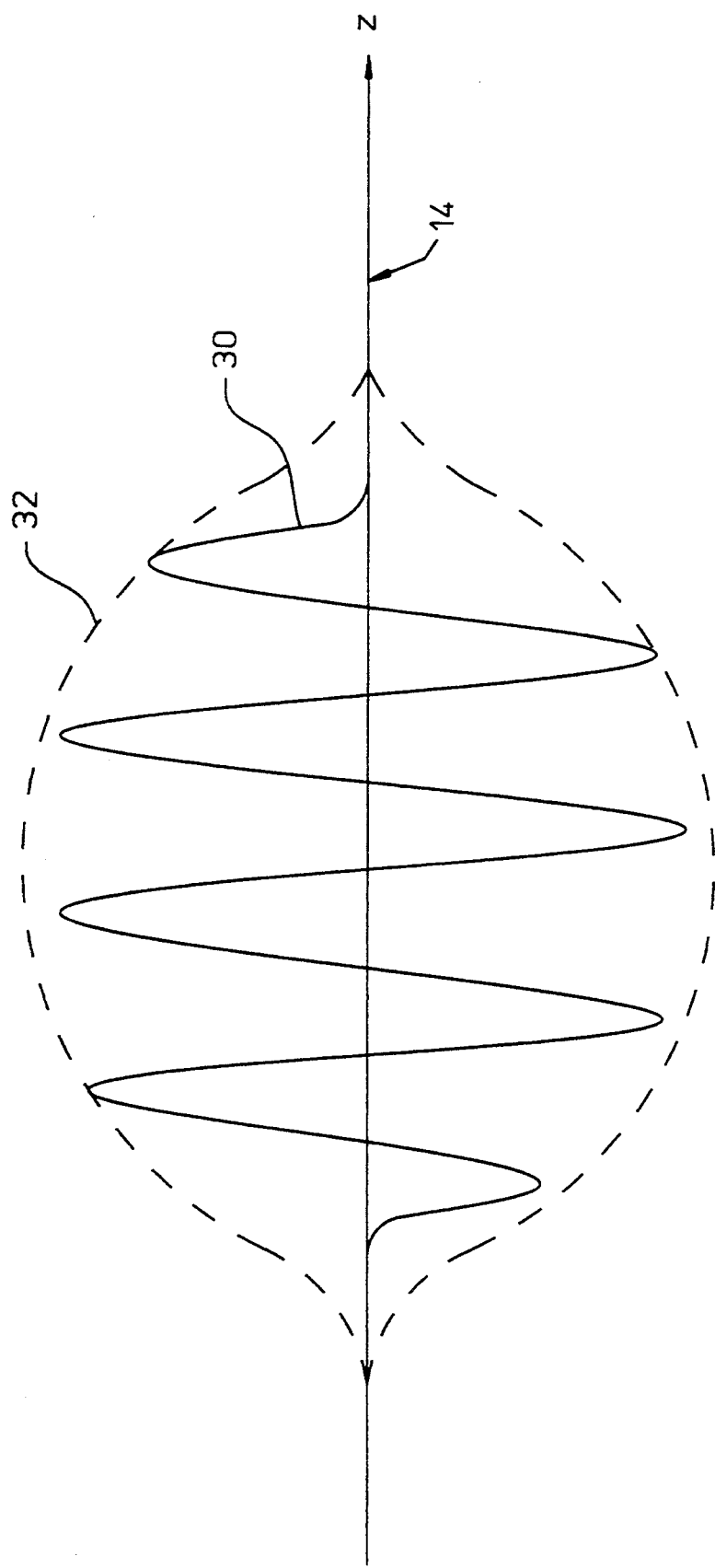
FIG. 3 illustrates a wave and envelope for a spherical interrogation volume (SIV) according to the invention.

FIG. 3 illustrates a wave and envelope for an SIV along the range direction. Four cycles of the pulse 30 define the wave envelope 32 along the range dimension of the SIV. In order to give the interrogation wave envelope the proper curvature along the z-axis, the amplitude of the pulse must increase from a minimum near the forward and rearmost points of the SIV to a maximum near the center of the SIV. The electrical transmit and receive signals needed to create the waveform for an SIV as shown in FIG. 3 can be determined by experiment or by theoretical calculations based on a knowledge of the physical properties of the chosen transducer elements in any given application.

Figure 4:
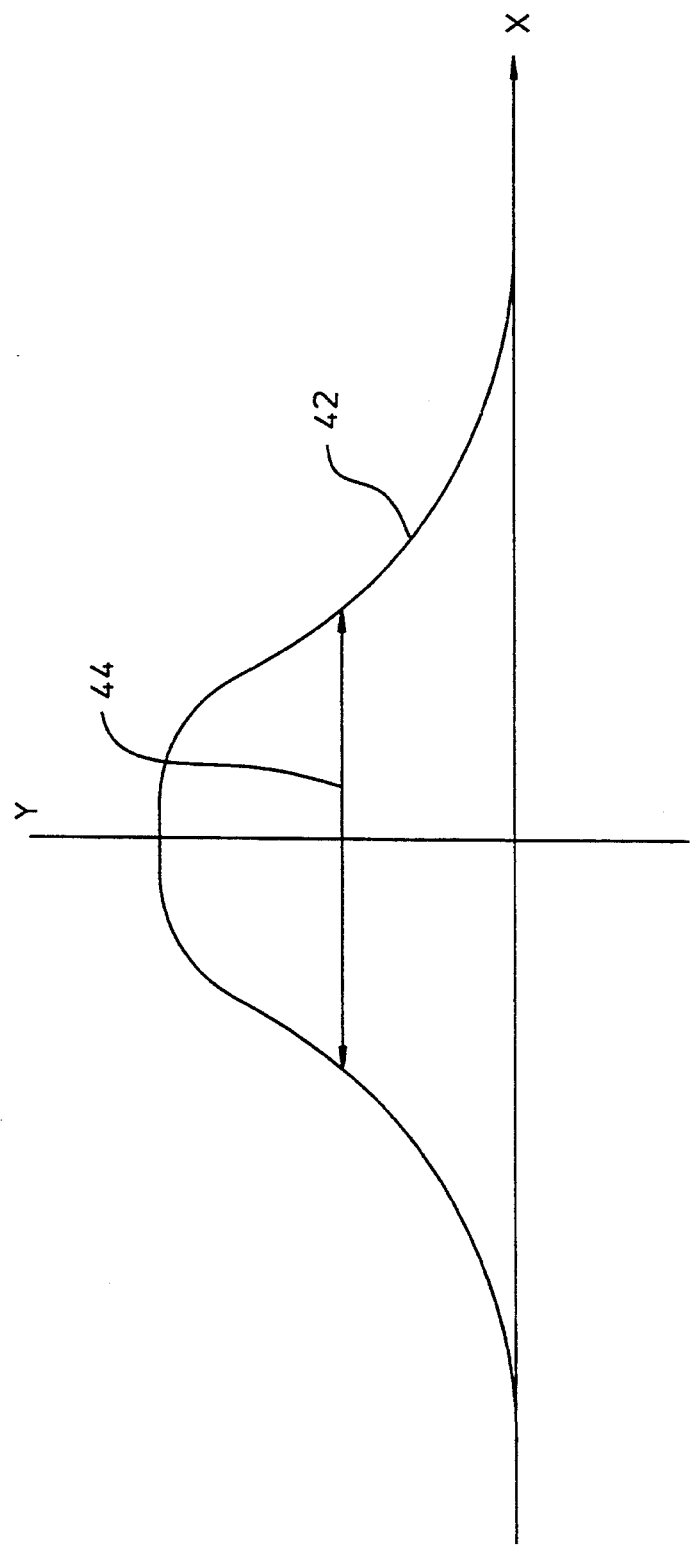
FIG. 4 illustrates a wave envelope for a SIV and an AIV along a lateral direction.

FIG. 4 illustrates a wave envelope for both an AIV and a SIV along a lateral direction. As FIG. 4 shows, the beam width for both interrogation volumes is limited by the focussing capability of the transducer. The double arrow 44 indicates the width of the wave envelope of the interrogation volume. For a perfect SIV according to this invention, the mean square gradient of the interrogation wave envelope in any direction through the center of the SIV remains the same (see Eqns. 7-9).

It will typically not be possible to create a perfectly spherical interrogation volume; rather, the interrogation volume may have a "tail" or "lip" along one or more of the axes. In general, however, as long as the interrogation volume is substantially spherical, the cross terms (see Eqn. 6) will still be small enough that they can be ignored without distorting the results significantly; in any event, the substantially spherical interrogation volume according to the invention will provide much greater direction independence than anisotropic interrogation volumes used in the prior art.

Experiments have indicated, for example, that a sufficiently spherical interrogation volume can be generated by creating a wave envelope with a Gaussian range profile of appropriate width. One should keep in mind that a spherical interrogation volume is a composite function of both the transmit and receive beam properties.

Figure 5:
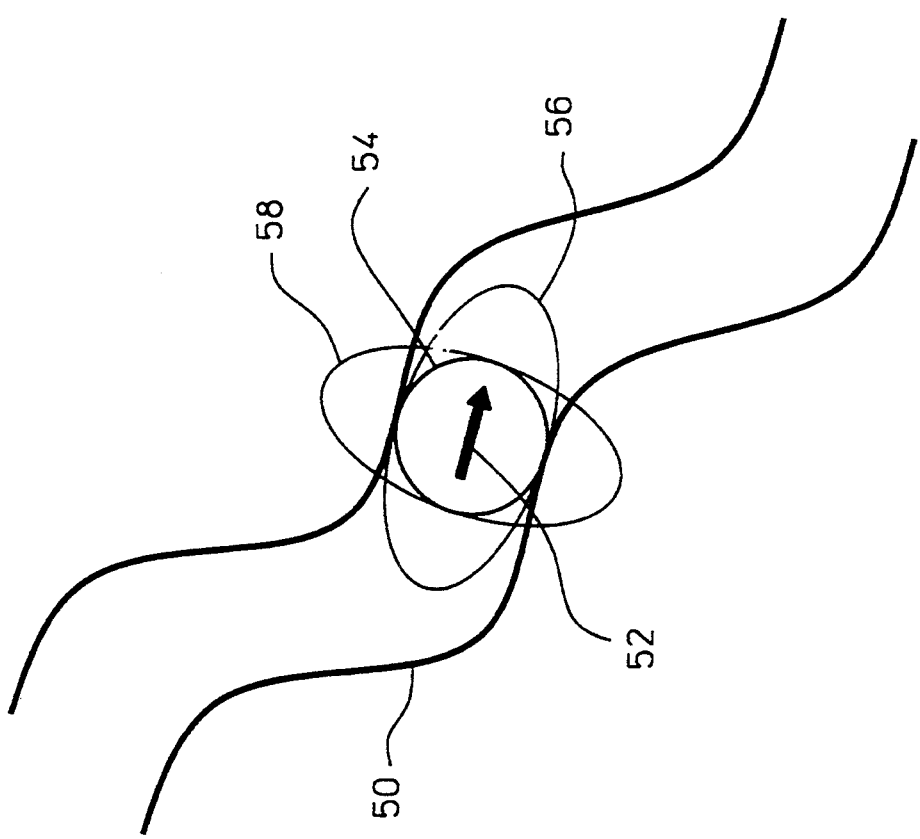
FIG. 5 illustrates a spherical interrogation volume in a blood vessel and two ellipsoidal interrogation volumes used to determined the direction of blood flow.

FIG. 5 illustrates the SIV according to the invention and also illustrates the method according to the invention for determining the direction of flow of blood within an artery 50. The local direction of flow of blood within the artery 50 is indicated by the arrow 52. FIG. 5 also shows a spherical interrogation volume 54 with the properties described above, which is focussed within the artery 50. As Eqns. 6–9 indicate, if the boundary of the interrogation volume is deformed so that the interrogation volume is ellipsoidal, a variation will be induced into the return signal so that the interrogation volume will become direction-dependent. The measured mean square rate of change of the envelope of the back-scattered return signal will then decrease as the direction of flow of the scattering particles within the fluid becomes more parallel to the long axis of the ellipsoid.

In FIG. 5, one ellipsoidal interrogation volume (EIV) 56 is shown with its long axis closely aligned with the direction of blood flow 52 while another EIV 58 is shown with its long axis nearly perpendicular to the direction of flow 52. The envelope of the return signal from the nearly perpendicular EIV 58 will show a much larger measured mean square rate of change than it will from the nearly aligned EIV 56. For any given eccentricity of the ellipsoid, it can be shown that the smallest mean square rate of change in the envelope occurs when the long axis of the ellipsoid is parallel to the direction of flow.

This invention takes advantage of this phenomenon and provides a method for determining the direction of blood flow within an interrogation volume as well as (or instead of) the magnitude of flow of the blood in the interrogation volume. If one first wishes to measure the flow magnitude, the ultrasonic array is first configured and excited so as to produce the SIV as described above and to focus it within the artery at a desired point of measurement.

As is well known, the ultrasonic signal that is back-scattered from within the interrogation volume is reconverted into an electrical signal because of the piezoelectric characteristics of the transducer elements, one or more of which may be used for the reconversion. Conventional processing circuitry is then used to sense and sample the analog signal from the selected transducer elements and to convert the signal into a digital form suitable for use in numerical calculations. The circuitry accumulates these measured values and calculates the mean square rate of change in the envelope of the return signal in order to determine flow magnitude using Eqn. 9.

The SIV is then "deformed" into an EIV by changing the phasing of the various transducer elements in the array used to generate the ultrasonic signal. Of course, one may also choose to forego the SIV step or to perform it last, in which case one generates the EIV at the start. The eccentricity of the EIV may be chosen by experiment or through calculations so that there is a large enough change in the returned mean square rate of change as the ellipsoid is rotated.

In general, the greater the eccentricity of the ellipsoid is, the greater will be the induced variation in the return signal; the ability to detect when the long axis of the now anisotropic, EIV is aligned with the direction of flow, will also increase. The physical configuration of the transducer array and the different possibilities for changing the relative phases of the various transducer signals will limit one's choices of eccentricity for the EIV's. If the center of the ellipsoid is at a region where there is great curvature in the artery, the long axis itself may extend over a region in which the direction of blood flow changes radically.

The ellipsoidal interrogation volumes preferably have the same center of focus as the SIV itself. This ensures not only that the same region of the artery is being measured, but also that the determination of flow direction will be from the same point as the magnitude determination made using the SIV.

The mean square rate of change of the envelope of the return signal for EIV's with the same center as the SIV (or as each other) is a function of the direction of the long axis of the ellipsoid and of the velocity of blood flowing through the EIV. Let $\bar{x}'=(x', y', z')$ be the direction of the long axis of the ellipsoidal interrogation volume. The mean square rate of change of the envelope of the returned ultrasonic signal can then be expressed as:

$$\overline{\left(\frac{\partial S}{\partial t}\right)^2} = g(\bar{x},\bar{v}) \qquad \text{Eqn. 10}$$

where g is a function of $\bar{x}'$ and $\bar{v}$, and where $\bar{x}'=(x', y', z')$ and $\bar{v}=(v_x, v_y, v_z)$.

Assume further that the flow velocity through the interrogation volume remains substantially constant as the EIV is rotated about its center point. In other words, assume that $\bar{v}$ is approximately constant. This means that Eqn. 10 can be further simplified such that the mean square rate of change of the envelope of the return signal is a function of the long axis direction $\bar{x}'$ alone.

By changing the phasing of the transducer array, the long axis of the EIV may be rotated about the center point of the ellipsoid. As the ellipsoid is rotated, the measured mean square rate of change will itself change and will reach a minimum when the long axis $\bar{x}'$ is parallel to the direction of flow. Since the mean square rate of change is a function of the three-dimensional vector $\bar{x}'$, any of a large number of known numerical optimization techniques, such as the Newton-Raphson techniques, may be used to control the manner in which the long axis is rotated in order to determine which orientation gives the minimum mean square rate of change. If the optimization method chosen requires one or more starting values for the vector $\bar{x}'$, these may be generated according to any known method, including simple random selection or arbitrary incremental changes in some predetermined direction.

As is mentioned above, known numerical techniques may also be used to calculate the mean square rate of change of the envelope of the return signal for any given interrogation volume. In order to determine the mean square rate of change, however, it will normally be necessary to sense many return signals in order to accumulate enough data points values to get a reliable estimate of the characteristics of the envelope, of the rate of change of the envelope, and of the mean of the square of the rate of change. The speed at which one can accumulate measurements will typically be the same as the pulse rate of the ultrasonic transducer array itself. For each of the ellipsoidal interrogation volumes, it will therefore be necessary to hold the volume fixed long enough to accumulate a sufficient number of measurements before taking the next step in the optimization routine, that is, before moving the EIV to a new orientation. The proper speed at which one rotates the ellipsoidal interrogation volumes may be determined by experiment and by incorporating any prior knowledge of the flow characteristics of the fluid.

Once the minimum value of the mean square rate of change of the envelope of the return signal is sensed, the direction of flow may be assumed to be the same as the direction of the long axis of the ellipsoid that provided the minimum value. Since this direction is known (x', y', z') as well as the center point of the ellipsoid (the focal point of the interrogation volume), one will have determined the direction of flow in that interrogation volume. If one has already measured this same region using the spherical interrogation volume, one will also have an accurate measure of the flow velocity. Of course, since the ellipsoidal interrogation volumes may be used to determine direction of flow (and thus the angle between the direction of flow and the line of sight or interrogation direction of the transducer array), normal Doppler techniques may then be applied regardless of the SIV in order to get an estimate of the flow.

Figure 6:
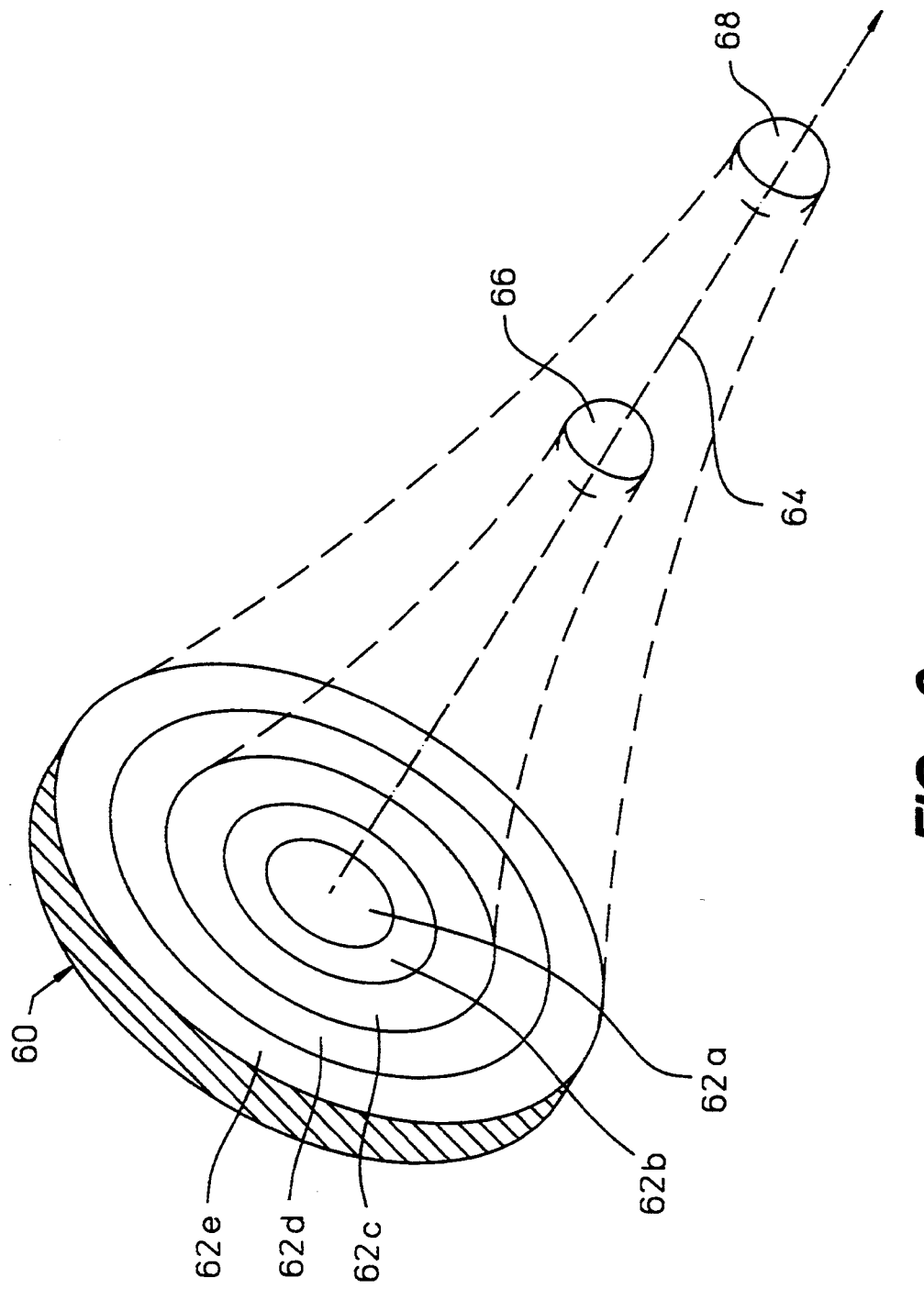
FIG. 6 illustrates an annular array of ultrasonic transducer elements that can be used to generate the SIV according to the invention.

FIG. 6 illustrates an array 60 of annular piezoelectric ultrasonic transducer elements 62a, 62b, 62c, 62d, and 62e. In the illustrated example, five annular transducer elements are shown, but more or fewer transducer elements may be used depending on the needs of any given application. For example, increasing the number of transducer elements while keeping the diameter of the array constant will in general increase the range over which equal-size spherical interrogation volumes may be produced, but it will also increase the complexity of the circuitry that excites and phases the various transducer elements. By increasing the diameter of the array 60, one creates a larger aperture and it then becomes possible to focus the interrogation volume farther away.

In the simplest case, the surface of the array 60 is substantially flat, although it is also possible to have a concave array and still be able to create a spherical interrogation volume. The annular array 60 generates interrogation volumes that are focussed on the line of the interrogation direction 64, which is substantially perpendicular to the array 60 and passes through its center point. The focal distance of the array 60 can be adjusted in a known manner by changing the number of transducer rings 62a-62e that are excited at the same time; starting with the two center transducer elements 62a, 62b, each time another concentric transducer ring is added, the aperture of the array 60 is increased. In FIG. 6, one SIV 66 is shown being generated by the three innermost transducer elements 62a-62c. Another SIV 68 that is farther away from the array 60 is created when all five transducer elements 62a-62e are excited.

The distance at which the interrogation volume is focussed is also a function of the relative delay of excitation of the various transducer elements. Delay focusing is known in the art and it is known that by changing the relative phasing of the signals from the transducer elements, the results of the constructive interference that arises moves the focus of the array in and out. Using a smaller aperture (fewer concentric annular transducer elements), one is able to focus at a shorter distance while still maintaining the same f-number. As is described above, the invention is unique compared to what is known in that it generates a stationary interrogation volume with a substantially constant mean square spatial gradient within the interrogation volume; the method according to the invention thereby allows for isotropic measurement of the flow.

Figure 7:
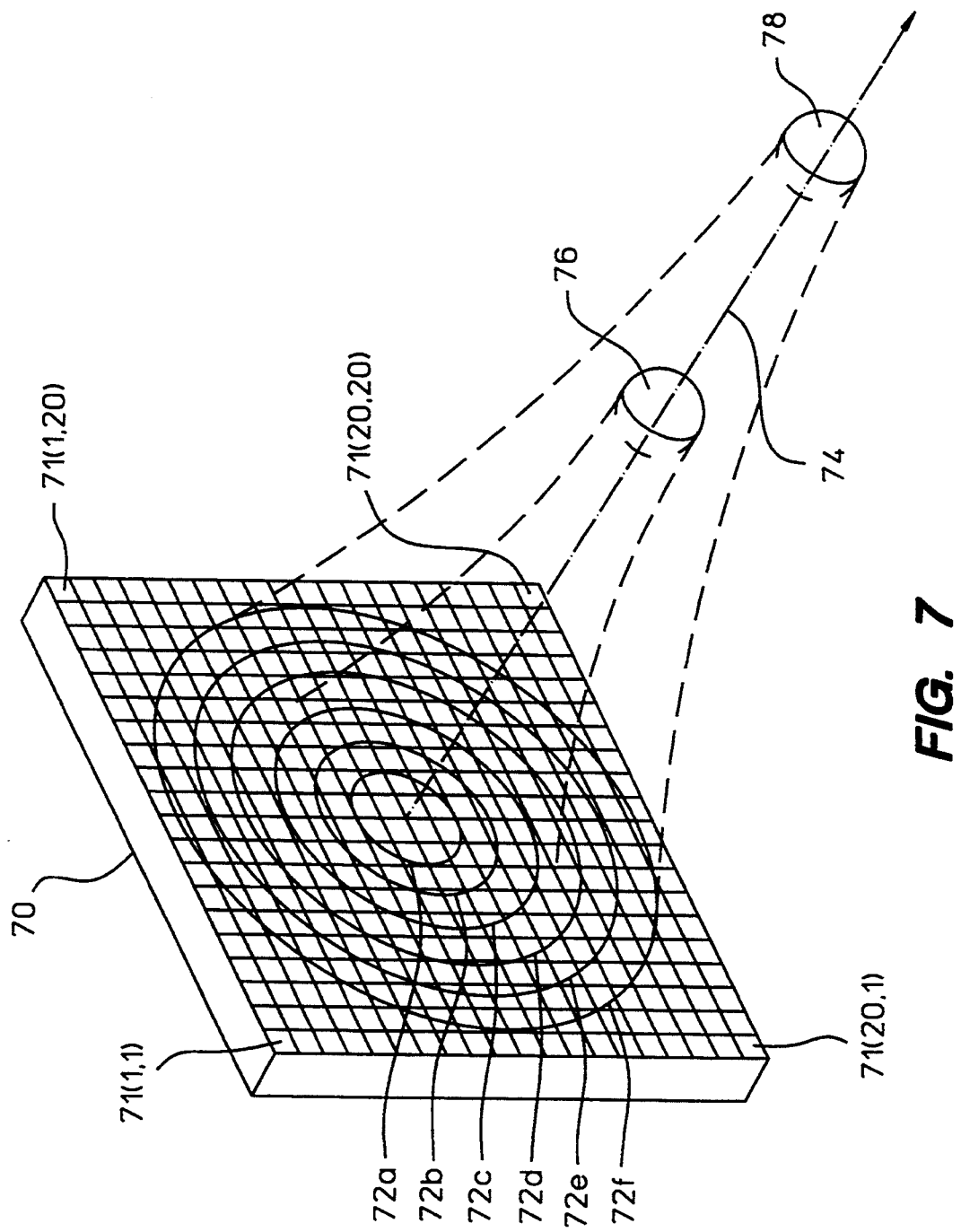
FIG. 7 illustrates a two-dimensional phased array of ultrasonic transducer elements that can be used to generate the SIV.

FIG. 7 illustrates a 2-D phased array 70 of ultrasonic transducer elements. In the illustrated example, the array consists of 400 transducer elements arranged as a 20-by-20 matrix, whose corner elements are labeled as 71(1, 1), 71(1, 20), 71(20, 1), and 71(20, 20). The number of transducer elements used in any given application will depend on the desired degree of beam-forming and other factors such as allowable manufacturing complexity and cost.

Concentric rings 72a-f are shown superimposed on the face of the array 70 only for the purpose of explanation. According to the invention, the individual transducer elements of the 2-D phased array 70 are excited in such a way that the array 70 can simulate a system of annular transducer elements, but is also able to simulate other apertures. In operation, in order to simulate the innermost transducer element (within the ring 72a), all of the transducer elements within the region marked by the ring 72a, or that have at least some predetermined portion within the ring, are excited simultaneously with substantially identical excitation signals. Similarly, any other annular region is simulated by exciting simultaneously those transducer elements that lie sufficiently within the corresponding annular region on the face of the array 70.

In the illustrated example, the 2-D phased array 70 is used to simulate on-axis focusing like that of the annular array shown in FIG. 6. Consequently, along the interrogation direction 74, different spherical interrogation volumes 76, 78 may be created depending on the diameter of the "aperture" created by the outermost simulated transducer "ring."

One of the advantages of the 2-D phased array 70 is that the number and diameters of the annular regions can be changed through a simple change in the electrical excitation signals, with no need for any mechanical changes. An additional advantage of the 2-D array 70 is that it also makes it possible not only to change the focal distance of the array but also to change the interrogation direction 74 and to modulate the eccentricity of the interrogation volumes. Depending on the physical properties of the transducer elements in the array 70, known analytical and numerical techniques, simulation, and experimentation can be used to determine excitation signals for the transducer elements that produce signals that constructively interfere to create and rotate ellipsoidal interrogation regions, as well as interrogation regions with other shapes.

Figure 8:
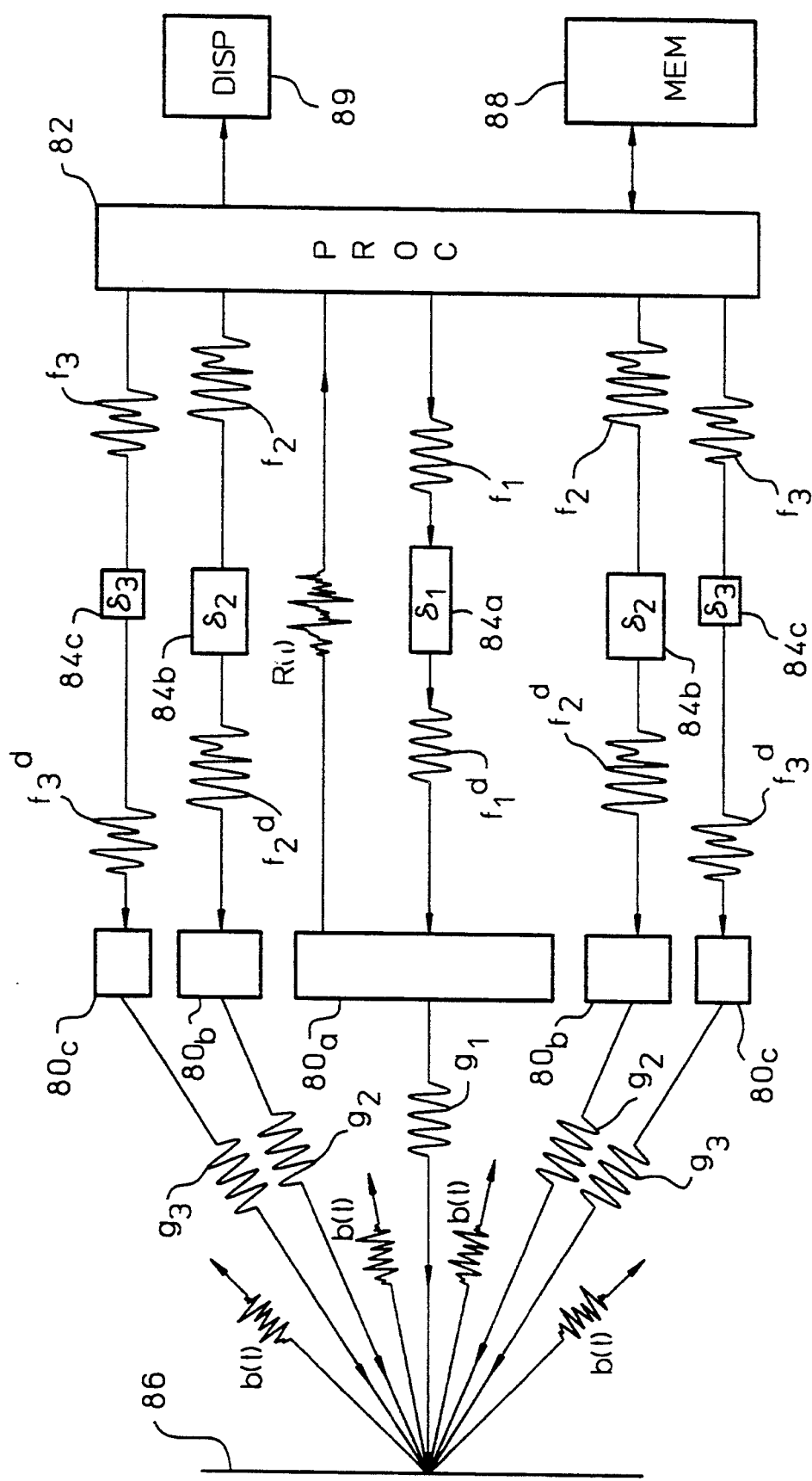
FIG. 8 shows a simplified block diagram of a system for generating the SIV using a three-ring annular array and the timing/phase relationships of the respective excitation signals for the different rings.

FIG. 8 is a schematic block diagram that shows the major components and signals of a system for measuring flow using an ultrasonic spherical interrogation volume. In FIG. 8, a simple 3-ring annular transducer array is shown only for purposes of easy explanation. In FIG. 8, the three elements of the array are labeled 80a, 80b, and 80c. Although a simple three-ring array is illustrated, the structure shown in FIG. 8 also applies in the more general case of a n-ring annular transducer array, or in the case of the 2-D phased array, for which the various excitation signals (described below) will be provided for each transducer in the array.

Conventional processing circuitry 82 generates electrical excitation signals $f_1$, $f_2$, $f_3$ as a sequence of pulses to drive the piezoelectric elements of the transducer array. In the simplest single-frequency or "monochromatic" case, each excitation signal will take the form $f_i(t) = E_i(t) \cdot \cos(\omega t)$. The excitation signals $f_1$, $f_2$, $f_3$ are time-delayed by amounts $\delta_1$, $\delta_2$, and $\delta_3$, respectively, either in separate conventional delay circuits 84a, 84b, 84c or by the processing circuitry 82 itself as it generates the excitation signals $f_1$, $f_2$, $f_3$. The different piezoelectric transducer elements 80a, 80b, 80c are excited by the respective delayed excitation signals $f_1^d$, $f_2^d$, $f_3^d$. Assuming that the excitation signals are single-frequency, the delayed excitation signals thus take the general form:

$$f_i^d = E_i(t) \cdot \cos[\omega \cdot (t - \delta_i)].$$

It is not necessary for the transducer excitation signals to be single-frequency; rather, as FIG. 8 shows for the excitation signals $f_2$ and $f_3$, the excitation signals may contain other frequency components so that the general form of the delayed excitation signals is:

$$f_i^d = (W_i, t, \delta_i)$$

where $W_i$ is a set of frequencies included in the spectrum of the respective excitation signal.

The transducer elements are excited by their respective input signals $f_i^d$ and emit corresponding ultrasonic output signals $g_1$, $g_2$, and $g_3$ that make up the interrogation signal and interfere with each other to focus the interrogation volume at a focal plane 86. Moving particles within the interrogation volume back-scatter the ultrasonic signal as a return signal $b(t)$. The back-scattered ultrasonic return signal is converted by one or more of the piezoelectric transducer elements 80a, 80b, 80c into the electrical return signal $R(t)$, which is a composite of the electrical return signals generated by each of the transducer elements in the array. After range gating and envelope detection, the mean square rate of change calculations are carried out in the processing circuitry 82. In a multi-element transducer, conventional beam-forming techniques are preferably used to combine the individual RF signals at each element into the composite RF signal $R(t)$ for range-gating and envelope detection.

The processing circuitry 82 may contain or be connected to conventional signal generation and conditioning circuitry in order to create the excitation signals $f_1$, $f_2$, $f_3$ as a sequence of pulses that are repeated at a predetermined rate. Similarly, the processing circuitry 82 may contain or be connected to conventional receiving and conditioning circuitry that carries out such functions as pre-amplification, sampling, and analog-to-digital conversion, which transforms the return signals, either individually or as the composite $R(t)$, from the transducer elements into numerical values suitable for use in the calculations of the mean square rate of change of the envelope of the composite return signal. The processing circuitry 82 or additional receiver circuitry may also be provided to achieve spherically symmetrical round-trip beam-forming in the interrogation volume.

A memory circuit 88 is either connected to or is contained within the processing circuitry 82. The memory circuit 88 is used to accumulate the successive values of the return signal (shown as the composite return signal $R(t)$ in FIG. 8) that are used to estimate the envelope of the return signal, which is in turn used in the differencing and averaging steps of the method according to the invention. The memory circuit 88 may also be used, for example, to digitally store signal profiles that the processing circuitry 82 uses to generate the excitation signals $f_1$, $f_2$, $f_3$. The flow magnitude or direction results may be displayed to the user on any conventional alphanumerical, graphical or other display device 89 that is driven by an output of the processing circuitry 82. The output results may also be passed on to additional processing, evaluation, or application circuitry.

The invention involves generating a spherical interrogation volume in order to determine flow magnitude independent of direction. The ultrasonic transducer output signals $g_1$, $g_2$, $g_3$ must therefore have signal forms that constructively interfere to create the spherical interrogation volume. In the preferred embodiment shown in FIG. 7 with the 2-D phased array, the excitation signals to the transducer elements may also have such signal waveforms that the constructive interference of the ultrasonic output signals from the transducer elements creates ellipsoidal interrogation volumes.

As is mentioned above, the envelope $E(t)$ of the output signals from the ultrasonic transducer elements is such that, for an SIV, the range dimension is set equal to the azimuth and elevation dimensions of the interrogation volume. In determining the output signals required from the various transducer elements, one must keep in mind that the envelope $E(t)$ of an output signal from a transducer will be substantially the same as the envelope of its excitation signal only if the transducer is sufficiently "fast." In general, however, the envelope of the output signal from a transducer element will not be the same as the envelope of the excitation signal that forms the electrical input to the piezoelectric transducer element.

The "slower" a transducer element is, the greater the degree of change will be, especially for input excitation signals that have more than one component frequency. As is well known, the characteristics of the output signal will depend on the impulse response characteristics of the corresponding transducer. Since one knows or can calculate the characteristics of the output signal that are required to generate the spherical or elliptical interrogation volumes according to the invention, it is possible to determine the required excitation signals either theoretically by deconvolution (assuming one knows or can estimate the impulse response function of each transducer), by simulation, or by experimentation. The parameters necessary to generate the corresponding signals may be stored in the memory circuit 88 for use by the processing circuitry 82 in generating the excitation signals $f_1$, $f_2$, $f_3$, not only for a given SIV, but also for the position in space of the SIV, or the position, orientation, and eccentricity of elliptical interrogation volumes.

We claim:

1. A method for measuring blood flow within a blood vessel or organ comprising the following steps:
   A. repeatedly applying to each of a plurality of piezoelectric transducer elements a corresponding pulsed electrical transmit signal;
   B. in the transducer elements, sensing a receive signal that is back-scattered from blood within the blood vessel;
   C. electrically shaping and phasing the transmit and receive signals to generate an interrogation signal within an interrogation volume, within which blood flow is to be measured;
   D. for each application of the pulsed electrical excitation signals, sensing an ultrasonic return signal that is back-scattered from particles within the interrogation volume;
   E. converting the sensed ultrasonic return signals into a corresponding composite electrical return signal;
   F. calculating an estimate of a mean square rate of change in time of an envelope of the composite electrical return signal; and
   G. outputting a representation of a predetermined blood flow characteristic as a predetermined function of the estimated mean square rate of change in time.

2. A method as defined in claim 1, in which the predetermined blood flow characteristic is the magnitude of flow velocity, comprising the following additional steps:
   A. shaping and phasing the electrical transmit and receive signals to the transducer elements so that the interrogation volume is substantially spherical and isotropic; and
   B. determining a proportionality factor equal to the mean square rate of change in space of the envelope of the return signal from the interrogation volume;
   in which the predetermined function of the estimated mean square rate of change in time used to calculate the magnitude of flow velocity comprises dividing the estimated mean square rate of change in time by the proportionality factor.

3. A method as defined in claim 2, in which the step of shaping and phasing the electrical transmit and receive signals includes generating the transmit and receive signals with mutual interference such that the mean square spatial gradient of the wave envelope is substantially constant within the interrogation volume.

4. A method as defined in claim 3, in which the step of shaping and phasing the electrical transmit and receive signals includes generating the interrogation volume with a range dimension substantially equal to an elevational dimension and an azimuthal dimension.

5. A method as defined in claim 1, in which the predetermined blood flow characteristic is the direction of blood flow, comprising the following additional steps:
   A. shaping and phasing the transmit and receive signals to the transducer elements so that the interrogation volume is substantially ellipsoidal with a long axis;
   B. generating a plurality of the ellipsoidal interrogation volumes with different directions of their respective long axes; and
   C. outputting as the representation of the flow direction the direction of the long axis of the ellipsoidal interrogation volume for which the estimated mean square rate of change in time of the envelope of the electrical return envelope signals is a minimum.

6. A method as defined in claim 5, in which the step of shaping and phasing the transmit and receive signals includes differential phasing of a plurality of transducer elements arranged as a two-dimensional phased array.

7. A method for measuring the magnitude of velocity of blood flow in a blood vessle or organ comprising the following steps:
   A. repeatedly applying to each of a plurality of piezoelectric transducer elements a corresponding pulsed electrical excitation signal;
   B. in the transducer elements, sensing a receive signal that is back-scattered from blood within the blood vessel or organ;
   C. electrically shaping and phasing the transmit and receive signals to generate a substantially spherical and isotropic interrogation volume within which blood flow is to be measured, with the mean square gradient of a wave envelope of the interrogation volume substantially constant;
   D. for each application of the pulsed electrical excitation signals, sensing an ultrasonic return signal that is back-scattered from particles within the interrogation volume;
   E. converting each sensed ultrasonic return signal into a corresponding electrical return signal;
   F. calculating an estimate of a mean square rate of change in time of an envelope of the electrical return envelope signals;
   G. determining a proportionality factor equal to the mean square rate of change in space of a wave envelope of the interrogation volume;
   H. calculating an estimate of a mean square rate of change in time of the envelope of the return signals; and
   I. outputting a representation of the magnitude of blood flow velocity corresponding to the estimated mean square rate of change divided by the proportionality factor.

* * * * *